(12) United States Patent
Bradley et al.

(10) Patent No.: US 6,711,439 B1
(45) Date of Patent: Mar. 23, 2004

(54) EVOKED RESPONSE VARIABILITY AS AN INDICATOR OF AUTONOMIC TONE AND SURROGATE FOR PATIENT CONDITION

(75) Inventors: Kerry Bradley, Glendale, CA (US); Euljoon Park, Stevenson Ranch, CA (US); Laurence S. Sloman, West Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 218 days.

(21) Appl. No.: 10/077,663

(22) Filed: Feb. 14, 2002

(51) Int. Cl.⁷ .............................................. A61N 1/362
(52) U.S. Cl. ........................................................ 607/9
(58) Field of Search ....................................... 607/4–30

(56) References Cited

U.S. PATENT DOCUMENTS 5,466,254 A    11/1995   Helland ..................... 607/123

*Primary Examiner*—Scott M. Getzow

(57) ABSTRACT

Modern implantable cardiac stimulation devices include processing and data storage capabilities that may be exploited to track myocardial condition and autonomic tone. Implantable devices have a capability to measure and store electrogram information over a period of time in a relatively large capacity memory, with advances in technology allowing increases in memory size. The evoked response varies in amplitude and morphology with changes in autonomic tone, ventricular filling, paced rate, and other parameters. The implantable cardiac device can be configured to sense and accurately quantify the evoked response, derive parameters from the quantified evoked response, store the parameters over long time periods, and derive variability statistics from the parameters to assist in tracking the patient's condition over time, and guiding the patient's therapy.

66 Claims, 6 Drawing Sheets

EVOKED RESPONSE VARIABILITY AS AN INDICATOR OF AUTONOMIC TONE AND SURROGATE FOR PATIENT CONDITION

BACKGROUND

1. Field of the Invention

Diagnosing a patient's condition is a challenging, time-consuming, and thus costly task for a health care supplier. Typically, condition is diagnosed and classified using electrocardiography or echocardiography testing. For example, evaluation of cardiomyopathy and assessment of ventricular systolic function are commonly undertaken by echocardiographic techniques that permit comprehensive assessment of left ventricular size and function.

2. Description of Related Art

M-mode echocardiography can be used to obtain precise measurements of left ventricular cavity size and wall thickness at end diastole and end systole but requires extensive procedures for preparation and measurement acquisition. Two-dimensional echocardiography is generally required to appropriately position the M-mode beam and to directly measure ventricular size, left ventricular volumes, ejection fraction, myocardial mass, and chamber volumes. A procedure that includes both two-dimensional and M-mode cardiography is generally required to obtain sufficient information to diagnose cardiomyopathy. High precision measurements are possible but require a high degree of care. Left ventricular mass and volume quantitation by echocardiography requires high-quality images, meticulous attention to proper beam orientation, and usage of accurate geometric models to approximate left ventricular shape.

M-mode echocardiography alone can be used to define many indices of global left ventricular function including ejection phase, fractional shortening of the minor axis, and circumferential fiber shortening velocity. However ejection fraction, the most common index, requires derivation using complex algorithms developed for volume determination from M-mode linear dimensions, visually estimated from two-dimensional echocardiographic images, or obtained by quantitative analysis of two-dimensional echocardiographic images. The algorithms vary greatly in complexity. These procedures are suitably accurate for normally-shaped, normally contracting left ventricles, but are deficient and require much more complex analysis for assessment of deformed ventricles with regional wall motion abnormalities, a not uncommon occurrence in myocardial patients.

These known diagnostic procedures are highly time-consuming, complex, and costly, requiring expensive diagnostic equipment and health provider time. What is needed is an accurate, automatic test capability that would allow tracking of myocardial condition outside the clinic.

SUMMARY

In one embodiment, an implantable cardiac stimulation device is disclosed that can be configured to sense and accurately quantify an evoked response resulting from an applied stimulation pulse, derive one or more parameters from the detected evoked response, store the one or more parameters over long time periods, and derive variability statistics from the one or more parameters to assist in tracking the patient's condition over time, which may be used to guide the patient's therapy.

An implantable cardiac stimulation device uses variation in cardiac evoked response as an indicator of autonomic tone. The cardiac stimulation device determines variability in one or more features derived from the evoked response in the time domain including amplitudes, slopes, integrals, time intervals, and any combination of parameters, or in the frequency domain. Frequency domain parameters include power in multiple frequency bands and ratios of power in the bands.

In accordance with one aspect, an implantable cardiac stimulation device comprises one or more pulse generators, one or more sensors, a data storage, a controller, and executable control logic that is capable of execution by the controller. The executable control logic derives at least one parameter from the sensed evoked response, determines variation of the at least one evoked response parameter over time, and derives an indicator of patient condition based on the parameter variation.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENT(S)

The following describes the best mode presently contemplated for practicing the invention. The description is not to be taken in a limiting sense but is set forth to convey the general principles of operation and structure of the illustrative embodiments. The issued claims define the invention scope. In the following description, like numerals or reference designators refer to like parts or elements throughout.

Figure 1:
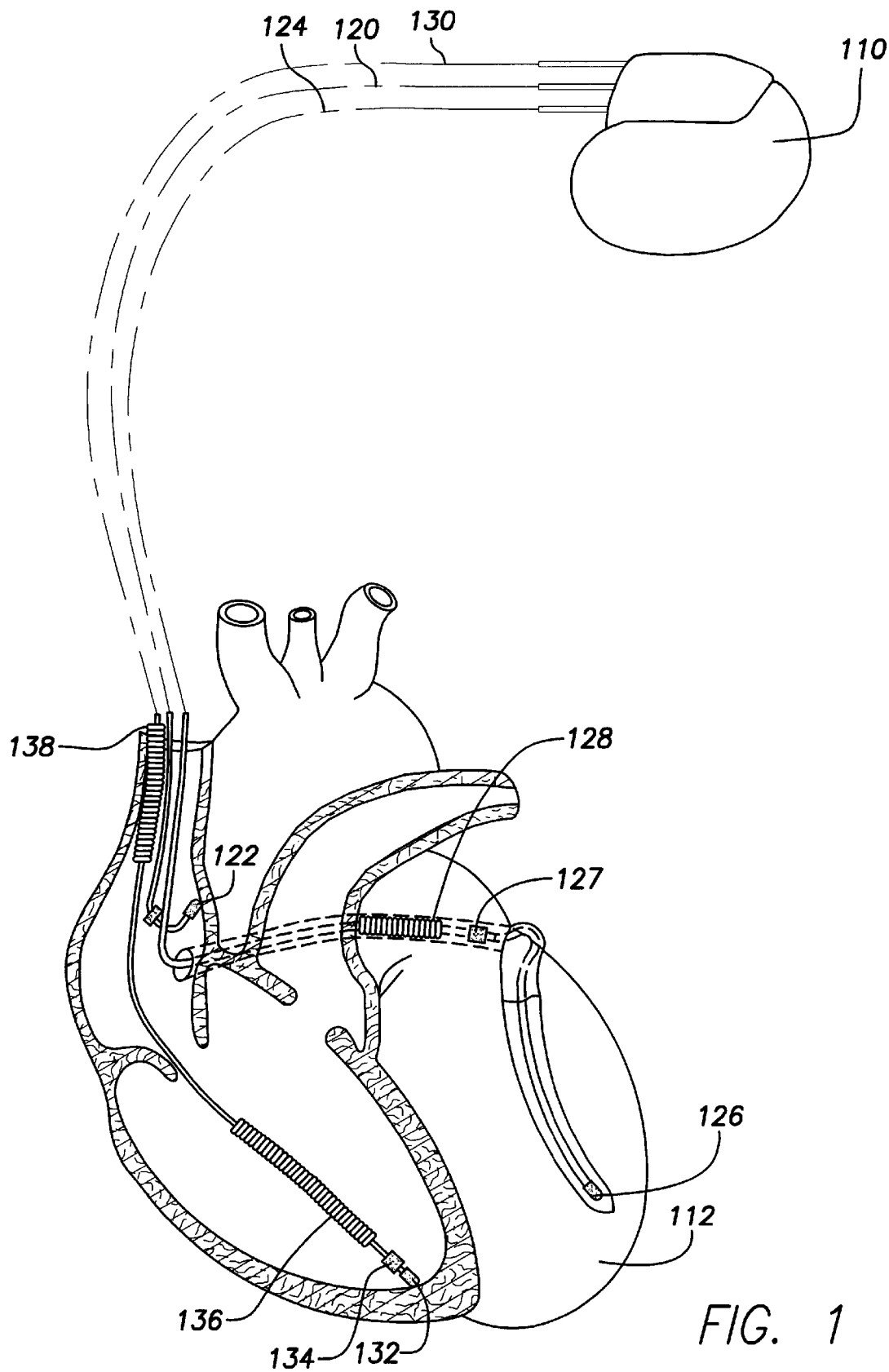
FIG. 1 is a simplified diagram illustrating an implantable stimulation device in electrical communication with at least three leads implanted into a patient's heart for delivering multi-chamber stimulation and shock therapy.

Referring to FIG. 1, a stimulation device 110 electrically couples to a patient's heart 112 using three leads 120, 124, and 130 to electrically communicate signals suitable for delivering multiple-chamber stimulation and shock therapy. The stimulation device 110 couples to an implantable right atrial lead 120 having at least an atrial tip electrode 122 to sense atrial cardiac signals and to supply right atrial chamber stimulation therapy. The atrial tip electrode 122 typically is implanted in the patient's right atrial appendage.

The stimulation device 110 is coupled to a "coronary sinus" lead 124 to sense left atrial and ventricular cardiac signals and to supply left chamber pacing therapy. The "coronary sinus" lead 124 is designed for placement in the "coronary sinus region" via the coronary sinus for positioning a distal electrode adjacent to the left ventricle and/or additional electrode(s) adjacent to the left atrium. The phrase "coronary sinus region" refers to the vasculature of the left ventricle including any portion of the coronary sinus, great cardiac vein, left marginal vein, left posterior ventricular vein, middle cardiac vein, and/or small cardiac vein or any other cardiac vein accessible by the coronary sinus.

The lead 124 may be used to supply stimulation pulses to a patient's left ventricle in biventricular pacing systems. Patients with chronic atrial fibrillation may be treated using biventricular VVIR pacemakers with left ventricular 124 and right ventricular 130 leads connected to the stimulation device 110. In patient's with spontaneous sinus rhythm, biventricular DDDR stimulating devices may be implanted with an atrial lead 120 placed in the upper right atrium and two ventricular leads 124 and 130 connected to the left and right ventricles, respectively.

An illustrative coronary sinus lead 124 is configured to receive atrial and ventricular cardiac signals and to deliver left ventricular pacing therapy using at least a left ventricular tip electrode 126. The coronary sinus lead 124 delivers left atrial pacing therapy using at least a left atrial ring electrode 127. The coronary sinus lead 124 delivers shocking therapy using at least a left atrial coil electrode 128. U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), that are hereby incorporated herein by reference, contain a complete description of a suitable coronary sinus lead.

FIG. 1 shows the stimulation device 110 electrically coupled with the patient's heart 112 by an implantable right ventricular lead 130. The right ventricular lead 130 in the illustrative embodiment has a right ventricular tip electrode 132, a right ventricular ring electrode 134, a right ventricular (RV) coil electrode 136, and an SVC coil electrode 138. Typically, the right ventricular lead 130 is transvenously inserted into the heart 112 to place the right ventricular tip electrode 132 in the right ventricular apex, positioning the RV coil electrode 136 in the right ventricle and the SVC coil electrode 138 in the superior vena cava. Inserted in this manner, the right ventricular lead 130 is capable of receiving cardiac signals and delivering stimulation in the form of pacing and shock therapy to the right ventricle.

Figure 2:
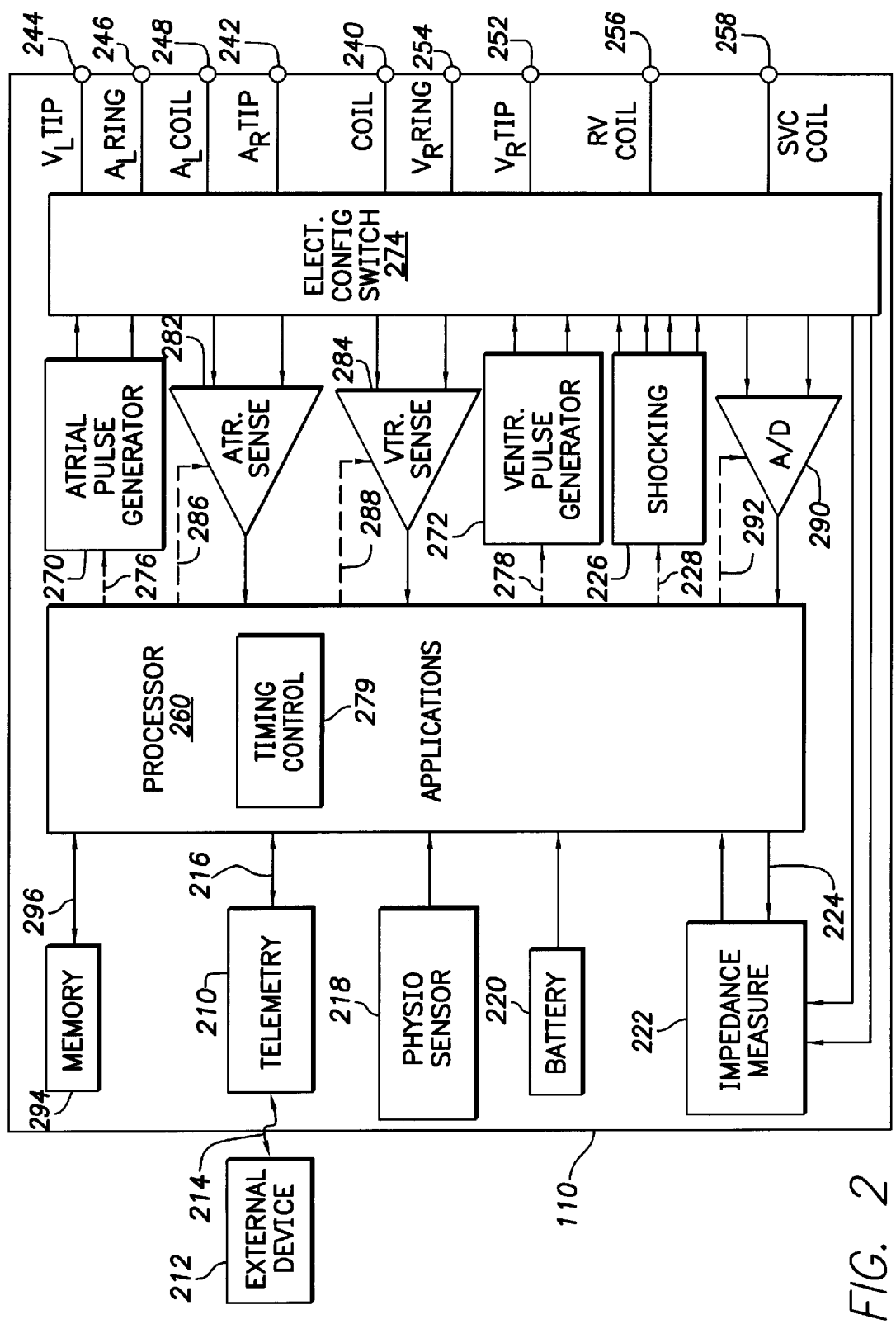
FIG. 2 is a functional block diagram that shows a multi-chamber implantable stimulation device illustrating basic elements of a stimulation device capable of cardioversion, defibrillation and pacing stimulation in four chambers of the heart.

Referring to FIG. 2, a simplified block diagram shows the multiple-chamber implantable stimulation device 110 that is capable of treating both fast and slow arrhythmias with stimulation therapy such as cardioversion, defibrillation, and pacing stimulation. The particular multi-chamber device is shown for illustration purposes only, and one of ordinary skill in the art can readily duplicate, eliminate, or disable various portions of circuitry in any desired combination to produce a device capable of delivering treatment in a desired chamber or chambers. Suitable treatments include, but are not limited to cardioversion, defibrillation and pacing stimulation, in either or both the atria and ventricles.

The housing 240 for the stimulation device 110, shown schematically in FIG. 2, is often referred to as the "can", "case" or "case electrode" and may be selected, for example by programming, to function as a return electrode for all "unipolar" modes. The housing 240 may also or otherwise be used as a return electrode alone or in combination with one or more of the coil electrodes, 128, 136 and 138, for delivering shocking stimulation to tissue. The housing 240 includes a connector (not shown) with a plurality of terminals 242, 244, 246, 248, 252, 254, 256, and 258. The terminals are shown schematically with, for convenience, names of the electrodes that are connected to the terminals shown next to the appropriate terminals. For example, at least a right atrial tip terminal ($A_R$ TIP) 242 is adapted for connection to the atrial tip electrode 122 to perform right atrial sensing and pacing.

To sense, pace, and shock in the left heart chambers, the connector includes at least a left ventricular tip terminal ($V_L$ TIP) 244, a left atrial ring terminal ($A_L$ RING) 246, and a left atrial shocking terminal ($A_L$ COIL) 248. The left ventricular tip terminal ($V_L$ TIP) 244 is adapted for connecting to the left ventricular ring electrode 125. The left atrial ring terminal ($A_L$ RING) 246 is configured to connect to the left atrial tip electrode 123. The left atrial shocking terminal ($A_L$ COIL) 248 is adapted to connect to the left atrial coil electrode 128.

The connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258 to support right chamber sensing, pacing and shocking. The right ventricular tip terminal ($V_R$ TIP) 252 is formed to connect to the right ventricular tip electrode 132. The right ventricular ring terminal ($V_R$ RING) 254 is adapted to connect to the right ventricular ring electrode 134. The right ventricular shocking terminal ($R_V$ COIL) 256 can connect to the $R_V$ coil electrode 136. The SVC shocking terminal (SVC COIL) 258 is configured to connect to the SVC coil electrode 138.

A programmable processor 260 is contained in the housing 240 and controls the various modes of stimulation therapy. The processor 260 can be implemented as any suitable control device such as a microcontroller, a controller, a microprocessor, a central processing unit, a signal processor, a digital signal processor, a state machine, a control logic, discrete control circuitry, or any similar control circuitry. In some embodiments, the processor 260 is designed specifically for controlling the delivery of stimulation therapy. The processor 260 may include RAM or ROM memory, logic and timing circuitry, state machine circuitry, and I/O circuitry. The processor 260 has a capability to process or monitor input signals or data, typically as a program code that is stored in a designated block of memory and executable by the processor 260. Details of design and operation of the processor 260 are well-known to those having ordinary skill in the art so that any suitable processor 260 may be used that can execute the functions described herein. Usage of microprocessor-based control circuits for performing timing and data analysis functions are well known by those having ordinary skill in the art.

Referring again to FIG. 2, an atrial pulse generator 270 and a ventricular pulse generator 272 generate pacing stimulation pulses that are delivered by the right atrial lead 120, the right ventricular lead 130, and/or the coronary sinus lead 124 via an electrode configuration switch 274. To therapeutically stimulate each of the four heart chambers, the atrial and ventricular pulse generators 270 and 272 may include dedicated, independent pulse generators, multiplexed pulse generators, or shared pulse generators. The processor 260 controls pulse generators 270 and 272 via appropriate respective control signals 276 and 278 to trigger or inhibit the stimulation pulses.

Processor 260 further includes timing control circuitry 279 to control timing of various stimulation pulse events such as pacing rate, atrio-ventricular (AV) delay, atrial interconduction (A—A) delay, or ventricular interconduction (V—V) delay, and others. The processor 260 and timing control circuitry 279 also track timing of refractory periods, blanking intervals, noise detection windows, evoked response windows, alert intervals, marker channel timing, and others. The timing control circuitry 279 times other various delays, event intervals, and timing windows that are well-known to those having ordinary skill in the art.

Switch 274 includes a plurality of switches for connecting the desired electrodes to the appropriate I/O circuits, allowing complete selective programming of electrode configuration. Typically, the processor 260 generates a control signal 280 that configures the switch 274 by selectively setting an appropriate combination of switches (not shown). In one example, the switches determine polarity of the simulation pulses from among possible unipolar, bipolar, combipolar polarities, and the like as are well-known to those having ordinary skill in the art.

Atrial sensing circuits 282 and ventricular sensing circuits 284 can detect cardiac activity in each of the four heart chambers by selective coupling to the right atrial lead 120, coronary sinus lead 124, and the right ventricular lead 130, through switch 274. The atrial (ATR. SENSE) 282 and ventricular (VTR. SENSE) 284 sensing circuits typically include amplifiers of various types such as dedicated sense amplifiers, multiplexed amplifiers, or shared amplifiers. The switch 274 determines sensing polarity of the cardiac signal by selectively configuring appropriate switches in a manner that is known to those having ordinary skill in the art. Stimulation and sensing polarity control is separate so that a clinician may program sensing polarity independently from programming of stimulation polarity.

The sensing circuits 282 and 284 each generally include one or more amplifiers, bandpass filtering, and a threshold detection circuit. Suitable amplifiers are precision amplifiers with programmable gain and/or automatic gain control functionality, a feature well-known to those having ordinary skill in the art. The sensing circuits 282 and 284 are programmed, either manually or automatically using a gain control algorithm to selectively sense a cardiac signal of interest. Automatic gain control enables the device 110 to effectively sense low amplitude cardiac signals, thereby managing the difficult problem of sensing low amplitude signal characteristics that occur in atrial or ventricular fibrillation conditions. Processor 260 receives output signals from atrial and ventricular sensing circuits 282 and 284. Processor 260 responds to the sensing signals by triggering or inhibiting atrial 270 and ventricular 272 pulse generators in the manner of "demand pacing" in response to the absence or presence of cardiac activity in the appropriate heart chambers.

Sensing circuits 282 and 284 receive control signals from processor 260 over signal lines 286 and 288 that control gain, threshold, polarization charge removal circuitry (not shown), and timing of any blocking circuitry (not shown) that is coupled to the input terminals of the sensing circuits 282 and 284. Gain, threshold, charge removal and blocking operations are well-known to those having ordinary skill in the art.

The device 110 performs arrhythmia detection utilizing the atrial and ventricular sensing circuits 282 and 284 to sense cardiac signals. In arrhythmia detection, the device 110 determines whether a rhythm is physiologic or pathologic. As used herein, the term "sensing" refers to monitoring of a cardiac signal for determining the presence of a cardiac pulse. The term "detection" refers to processing of the sensed cardiac signals to determine the presence of an arrhythmia. Processor 260 classifies cardiac signals by comparing timing intervals between sensed events to a predefined rate zone limit and analyzing other characteristics to determine an appropriate remedial therapy. Measured and monitored timing intervals between sensed events include P-waves, R-waves, and depolarization signals associated with fibrillation which are sometimes referred to as "F-waves" or "Fib-waves", such as "atrial Fib-waves" and "ventricular Fib-waves". The timing intervals are compared to a predefined rate zone limit such as bradycardia, normal, low rate VT, high rate VT, fibrillation rate zones, and other rate limits that are known to those having ordinary skill in the art. Other analytical characteristics are selected from among, but not limited to sudden onset, stability, physiologic sensors, and morphology. The device 110 delivers remedial therapies such as bradycardia pacing, anti-tachycardia pacing, cardioversion shocks or defibrillation shocks, collectively referred to as "tiered therapy".

An analog-to-digital (A/D) data acquisition system 290 also receives cardiac signals for acquisition, conversion, and storage or communication. The data acquisition system 290 is configured to acquire intracardiac electrogram signals in analog format, convert the raw analog data into a digital signal, and store the digital signals for later processing and/or telemetric transmission to an external device 212. The data acquisition system 290 couples to the right atrial lead 120, the coronary sinus lead 124, and the right ventricular lead 130 through the switch 274 to acquire cardiac signal samples across any desired pair of electrodes.

In an illustrative system, the data acquisition system 290 can operate in cooperation with the processor 260 or other detection circuitry to assist in detection of capture in response to an applied stimulus. Capture is defined as stimulation sufficient to cause the heart muscle to contract. The device 110 generates and applies an electrical stimulus to the heart with sufficient energy to depolarize the cardiac tissue, causing heart muscle contraction. The processor 260 monitors the cardiac signal during a selected time window following a stimulation pulse. Occurrence of a depolarization signal in the window indicates successful capture. The processor 260 enables capture detection by triggering the ventricular pulse generator 272 to generate a stimulation pulse, starting a capture detection window using the timing control circuitry 279 within the processor 260, and enabling the data acquisition system 290 via control signal 292. The data acquisition system 290 samples the cardiac signal during the capture detection window and, based on signal amplitude, determines whether capture has occurred.

The device 110 can be configured to perform capture detection on a beat-by-beat basis or on a sampled basis. Typically, the device 110 performs a capture threshold search once per day during at least an acute phase, for example the first 30 days after implant, and less frequently thereafter. A capture threshold search begins with the stimulus amplitude set at a desired starting point, either a high energy level or the level at which capture is currently occurring, and the energy level decreases in steps until capture is lost. The capture threshold is the energy value at which capture is lost. The stimulus energy level is set to the capture threshold plus a safety margin.

The processor 260 is coupled to a memory 294 by a suitable data/address bus 296. Memory 294 stores programmable and/or automatically-determined operating parameters used by the processor 260. Operating parameters are stored, determined, or modified, to customize the operation of the stimulation device 110 to needs of a particular patient. The operating parameters define, for example, pacing pulse amplitude, pulse duration, electrode polarity, stimulation rate, sensitivity, automatic features, arrhythmia detection criteria, and stimulation pulse characteristics. Stimulation pulse characteristics include amplitude, waveshape, and vector of each shocking pulse to be delivered to the patient's heart 112 within particular tiers of therapy. A feature of the device 110 is a capability to sense and store a relatively large amount of data, for example acquired from the data acquisition system 290. The data may then be used for subsequent analysis to guide device programming or to automatically adjust operational control.

Operating parameters of the implantable device 110 may be non-invasively programmed into the memory 294 through a telemetry circuit 210 in telemetric communication with the external device 212, such as a programmer, transtelephonic transceiver, or a diagnostic system analyzer. The processor 260 sends a control signal 216 that activates the telemetry circuit 210. The telemetry circuit 210 communicates intracardiac electrograms and status information relating to the operation of the device 110 to the external device 212 through an established communication link 214.

In some embodiments, the stimulation device 110 can include a physiologic sensor 218, commonly called a "rate-responsive" sensor that is typically used to adjust pacing stimulation rate according to the exercise state of the patient. The physiological sensor 218 may also be used to detect changes in cardiac output, changes in the physiological condition of the heart, or diurnal changes in activity such as detecting sleep and wake states. The processor 260 responds by adjusting various pacing parameters such as rate, AV Delay, V—V Delay, and the like, at which atrial and ventricular pulse generators 270 and 272 generate stimulation pulses.

Although the example shows the physiological sensor 218 included within the stimulation device 110, the physiologic sensor 218 may otherwise be located external to the stimulation device 110. An external physiological sensor 218 may be implanted within a patient or carried by the patient. A common type of rate responsive sensor is an activity sensor such as an accelerometer or a piezoelectric crystal, mounted within the housing 240 of the stimulation device 110. Multiple other types of physiologic sensors are suitable, including for example sensors that measure blood oxygen content, blood pH, respiration rate and/or minute ventilation, ventricular gradient, and other parameters. Generally any sensor capable of sensing a physiological parameter that corresponds to the exercise state of the patient may be used.

The stimulation device 110 includes a battery 220 that supplies operating power to all of the circuits shown in the device 110. For a stimulation device 110 that is capable of delivering a shocking therapy, a suitable battery 220 is capable of operating at low current drains for long periods of time, but also be capable of generating high-current pulses for capacitor charging when the patient requires a shock pulse. A suitable battery 220 has a predictable discharge characteristic so that elective replacement time can be detected. Most typically, the device 110 employs lithium/silver vanadium oxide batteries for most, if not all current devices.

The device 110 also has an impedance measuring circuit 222 which is enabled by a control signal 224 from the processor 260. The impedance measuring circuit 222 is useful for one or more of several functions. The impedance measuring circuit 222 performs lead impedance surveillance during the acute and chronic phases for proper lead positioning and detection of lead dislodgment. The impedance measuring circuit 222 permits detection of electrode operability and automatic switching from an inoperable pair to an operable pair if dislodgment occurs. Impedance measuring circuit 222 is useful for measuring respiration or minute ventilation that can be applied to rate responsive pacing or other automatic control operations. The impedance measuring circuit 222 can be configured to measure thoracic impedance to determine shock thresholds. Impedance measurements can be used to detect implant time of the device 110. The impedance measuring circuit 222 can be used for many other various operations including measurements of stroke volume, detection of heart value opening, and the like. The impedance measuring circuit 222 can be coupled to the switch 274 so that any desired electrode may be used.

In some embodiments, the stimulation device 110 is configured to operate as an implantable cardioverter/defibrillator (ICD) device. An ICD device detects arrhythmia conditions and responds to the detected arrhythmia condition by automatically applying a suitable electrical shock therapy to the heart for the purpose of terminating the detected arrhythmia. The processor 260 controls a shocking circuit 226 by way of a control signal 228. The shocking circuit 226 generates shocking pulses of low (up to 0.5 Joules), moderate (0.5–10 Joules), or high energy (11 to 40 Joules), under control by the processor 260. Shocking pulses are applied to the patient's heart 112 through at least two shocking electrodes, selected from the left atrial coil electrode 128, the RV coil electrode 136, and/or the SVC coil electrode 138. The housing 240 may be used as an active electrode in combination with the RV coil electrode 136, or as part of a split electrical vector using the SVC coil electrode 138 or the left atrial coil electrode 128, for example using the RV electrode as a common electrode.

Cardioversion shock energy is a relatively low to moderate energy level to reduce pain felt by the patient. The cardioversion shock can be synchronized with an R-wave cardiac signal and can be part of tachycardia treatment. Defibrillation shock energy is generally a moderate to high energy level, for example corresponding to thresholds in the range of 5–40 Joules, and is delivered asynchronous with respect to intrinsic cardiac activity since R-waves may be insufficiently organized for synchronous stimulation utility. Defibrillation shocks are applied exclusively to treatment of fibrillation. Processor 260 is capable of controlling the synchronous or asynchronous delivery of the shocking pulses.

Figure 3A:
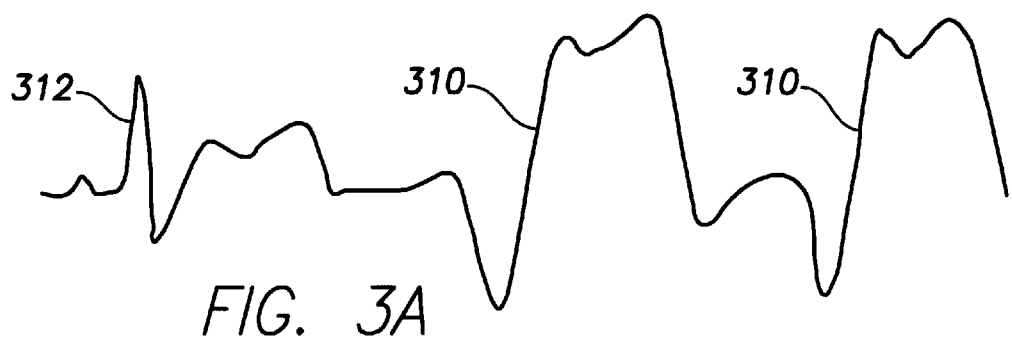
FIGS. 3A and 3B are two graphs that illustrate examples of time waveforms respectively showing a unipolar ventricular evoked response and a bipolar ventricular evoked response that may be sensed and quantified using the stimulation device.
Figure 3B:
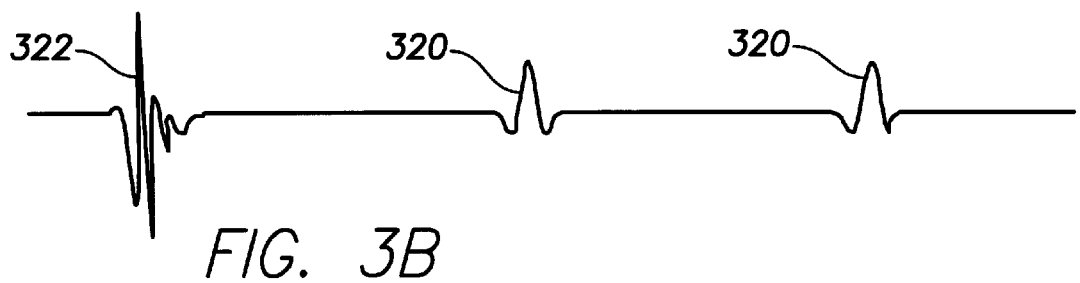

Referring to FIGS. 3A and 3B, two graphs illustrate examples of time waveforms respectively showing a unipolar atrial evoked response 310 and a bipolar atrial evoked response 320 that may be sensed and quantified using the stimulation device 110. Although analysis of evoked potentials is possible using either unipolar or bipolar sensing, unipolar sensing from tip electrode to case produces an evoked potential with a wider and more distinct morphology.

FIG. 3A shows a sequence of heartbeats in which a series of unipolar atrial evoked potentials 310 follows an intrinsic atrial depolarization, called a P-wave 312. FIG. 3B shows a similar sequence of heartbeats in which a series of bipolar atrial evoked potentials 320 follows an intrinsic atrial P-wave 322.

The disclosed stimulation device 110 acquires cardiac evoked response data, monitors and detects changes in the evoked response data over time, and uses variation in the cardiac evoked response as an indicator of autonomic tone and myocardial state. In various embodiments and applications, evoked response data may be acquired from either or both the atria and ventricles, and may be measured either by endocardial or epicardial sensing. Typically, the stimulation device 110 operates as a cardiac monitor from one location, for example, the atrium, left ventricle, or right ventricle.

Efficacy of evoked response signals is affected by selection of suitable leads 120, 124, and 130. Leads constructed from titanium nitride are highly suitable for evoked response sensing and analysis, although other types of leads including platinum, platinum black, platinum iridium, pyrolite carbon, and others may also be suitable.

For acquisition of evoked response data, the sensing circuits 282 and 284 may be adjusted to improve signal quality. Bandwidth may be adjusted by controlling bandpass filtering parameters to acquire lower frequency signals and detect the lower frequency content of the evoked response signal. For example, the lowpass cutoff frequency may be changed from approximately 1 Hz to 0.5 Hz.

The stimulation device 110 acquires and monitors one or more of several features derived from evoked potential measurements or data. Evoked potential features include data derived from time domain measurements and frequency domain parameters. Examples of time domain features include amplitudes, slopes, integrals, time intervals, and combinations of the listed features. Examples of frequency domain features include power, power levels in particular frequency bands, and ratios of power levels in different frequency bands. Frequency domain parameters may be derived from single evoked response complexes, ensemble-averaged complexes, and/or periodograms of stored intracardiac electrograms (IEGM) containing only evoked response measurements. The frequency domain parameters are derived over a specified time period.

The derived evoked potential or evoked response parameters are used as indicators of a patient's autonomic tone and thus are useful as a surrogate for patient condition. The stimulation device 110 monitors the evoked response parameters to determine progression or regression of cardiac disease, and to manage therapy such as a pacing therapy to enhance operation of the myocardium.

In one application, the stimulation device 110 derives a parameter indicative of conduction velocity of underlying paced myocardial tissue. For a unipolar evoked response, a time potential waveform is acquired and analyzed to determine the time interval from the stimulus to a potential zero-crossing of the depolarization portion of the acquired cardiac evoked potential.

For a bipolar evoked response, a time potential waveform is acquired and analyzed to determine slope of the evoked potential waveform. The unipolar time-to-zero-crossing parameter and the bipolar slope parameter are strongly correlated to conduction velocity of paced myocardial tissue. Myocardial tissue conduction velocity is directly modulated by the autonomic nervous system (ANS) and is indirectly modulated by circulating catecholamines. Measurement of variability of parameters such as the unipolar time-to-zero-crossing parameter and the bipolar slope parameter over time is a metric of ANS effects on myocardial state.

In another application, the stimulation device 110 may acquire unipolar ventricular evoked response data and determine the positive slope value of the evoked response waveform. The positive slope may be used to estimate a conduction velocity measurement since the evoked response results from propagation of a depolarization wavefront away from a stimulating electrode. The wavefront may be modeled as a moving dipole in which the potential at a measurement electrode, which may also be the stimulating electrode, is inversely related to the conduction velocity of the myocardial tissue. For an increased conduction velocity, the evoked response slope increases. For a decreased conduction velocity, the evoked response slope decreases.

Another parameter indicative of autonomic nervous system tone is evoked response amplitude. Evoked response amplitude is correlated to conduction velocity in myocardial cells, to the number of cells active in the active region of myocardium, and to catecholamine levels in the vicinity of the myocardial tissue. Intracellular resistivity of myocardial cells is inversely related to the square of the conduction velocity. Because transmembrane current is proportional to the spatial derivative of the intracellular current, transmembrane current is also proportional to conduction velocity. The evoked response is an extracellular potential and is thus proportional to the conduction velocity by the integral of the transmembrane current over the volume of tissue beneath the electrode. Accordingly, an increased conduction velocity generates larger evoked responses. An increased number of active cells in the vicinity of the sensing electrode and increased catecholamine levels in the myocardial vicinity also increase evoked response amplitude. Amplitude of the evoked response may thus be used as a surrogate for myocardial state.

The evoked response amplitude and evoked response integral may also be used to estimate end systolic volume, and allow adaptation of therapy based on the measurements of end systolic volume.

In patients with heart failure, long-term monitoring of evoked response amplitude, slope, integral, and other parameters permits tracking of progression and regression of heart condition with, for example, a reduction in amplitude being indicative of heart failure progression.

The stimulation device 110 uses several parameters for controlling stimulation operations. Pacing parameters include cardiac rate or stimulation rate, and the delay interval between atrial and ventricular activity, either atrioventricular delay (AV-delay) or P-wave to ventricular delay (PV-delay), as well as V—V delay. These parameters affect evoked response characteristics including the diagnostic test data. To account for variability in stimulation parameters, the stimulation device 110 monitors and records the rate and AV/PV-delay information in combination and simultaneously with information derived from the evoked response. Variability in evoked response features may be corrected for rate and atrioventricular delay conditions during interpretation of evoked response variability parameters.

Other conditions that may vary evoked response characteristics include activity level and chronotropic effect. Although not required for analysis of myocardial condition, the stimulation device 110 may include an activity sensor that measures a parameter such as motion, respiration, QT interval, and the like that is indicative of either a resting state or a state of exercise or activity. A stimulation device 110 typically includes a clock or timer that monitors cardiac rate including both intrinsic and paced heartbeats. The stimulation device 110 may be controlled to interrupt detection and analysis of evoked potentials when the activity sensor indicates activity above a preselected threshold level, and when the cardiac rate or AV/PV-delay are outside a specified range.

The stimulation device 110 monitors the evoked response over time as a surrogate of heart condition to detect progression or regression in heart failure patients. Evoked response monitoring tracks long-term changes in myocardial condition while filtering circadian and other extraneous influences on measurements such as cardiac rate, exercise or activity level, and time of day. The stimulation device 110 may also filter measurements that are out-of-range in comparison to the most recent history of measurements.

The surrogate indication of heart condition permits monitoring of heart failure without use of direct hemodynamic measurements such as cardiac output, stroke volume, and left ventricular pressure that require special sensors.

The stimulation device 110 is configured to automatically measure and track myocardial condition over time using a diurnal sensor that triggers a measurement at a consistent, suitable time at regular intervals such as one or more times per day or week. In one example, a daily measurement may be performed. In another example, a 24-hour histogram may be acquired. Daily changes in autonomic tone are monitored by analysis of histogram characteristics such as width and tendency of the histogram at the same time of the day.

Monitored evoked response variation parameters may be stored internally in the stimulation device 110, for example in RAM or ROM memory of processor 260 or memory 294, for retrieval at follow-up to guide physician therapy. In various applications, conduction velocity measurements and estimations may be used to evaluate autonomic nervous system tone as it affects the myocardium. Conduction velocity measurements may also be used to assess effectiveness of drug therapy administered by the physician. The physician may use the evoked response variation data to manage drug dosages, such as dosage of beta blockers, and to direct stimulation therapy, such as determination of application of ablation therapy.

In other applications, the evoked response variation data may be used independently by the stimulation device 110 to automatically adjust device therapy. In one example, the evoked response variation data may be used to titrate aggressiveness of overdrive pacing or allowing the device to program lower circadian rates or longer AV/PV-delay intervals to allow more intrinsic cardiac activity, or to adjust V—V timing.

For example, the stimulation device 110 may also be controlled to monitor evoked response parameters in combination with cardiac rate and AV/PV-delay settings to optimize stimulation rate and AV/PV-delay to attain a desired autonomic tone, and/or to optimize V—V timing.

Figure 4:
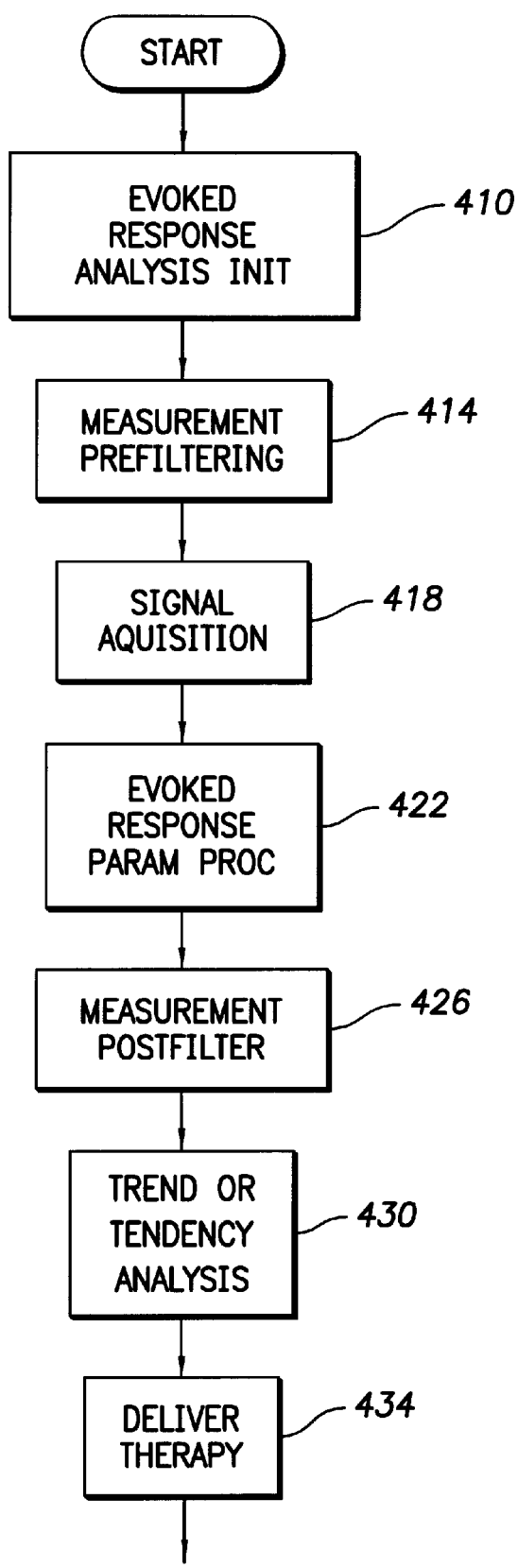
FIG. 4 is a highly schematic flow chart that describes actions that are performed by various embodiments of a stimulation device that includes functionality for monitoring and analyzing evoked response information.

Referring to FIG. 4, a flow chart describes an overview of the operation and features implemented in one embodiment of the device 110. In the flow chart, and the additional flow charts described herein, the various acts are summarized in individual "blocks". The blocks describe specific actions or decisions that are made or performed as the operation proceeds. Where a processor or equivalent element is employed, flow charts presented herein describe operations of a "control program" that may be used by such a processor or equivalent element to effectuate desired control of the stimulation device. Those having ordinary skill in the art can readily write such a control program based on the flow charts and other descriptions presented herein.

The highly schematic flow chart describes actions that are performed by various embodiments of a stimulation device 110 that includes functionality for monitoring and analyzing evoked response information. The processor 260 begins an evoked response analysis initiation operation 410 that sets stimulation and operational parameters to prepare for evoked response acquisition and analysis. For example, AV-delay is typically set to a short interval, such as 50 ms, to stimulate ventricular activity before an intrinsic pulse occurs. For a monitoring regimen that samples once per day, the reduced AV-delay is used to invoke the single measurement.

In a measurement prefiltering operation 414, the processor 260 checks operational parameters that may be selected from among cardiac/stimulation rate, AV/PV-delay, and other suitable parameters. If operational parameters are in a suitable range, environmental or other conditions may be checked.

A real-time clock (not shown) tracks time-of-day. If the time is selected to be an appropriate tracking time, the processor 260 may check environmental conditions using sensors indicative of exercise or activity, for example sensors of motion, respiration, QT interval, and the like. If the sensor reading is indicative of an exercise or noisy condition, analysis is typically delayed to avoid incorrect or misleading measurement results.

In a signal acquisition operation 418, the analog-to-digital (A/D) data acquisition system 290 samples the evoked response following a stimulation pulse and the samples are stored, for example in the memory 294.

In an evoked response parameter processing operation 422, the processor 260 determines one or more evoked response parameters by performing analysis operations on samples stored in the memory 294. The evoked response parameter processing operation 422 may include a filtering operation, if needed to reduce noise variations in the evoked response signal. An amplitude parameter is typically determined by peak detection of either negative or positive signal excursions of filtered or unfiltered evoked response signals. Slopes are typically determined by differentiating the evoked response signal. A slope parameter may be selected to be a maximum positive or negative slope, a derivative detected at a particular position on the evoked response waveform, a derivative at a selected time following the stimulus, or the like.

Evoked response integral parameters are typically summations of several time samples in the evoked response waveform, and may be the integral of negative waveform samples, positive waveform samples, or a combination of positive and negative waveform samples. Integrated samples may be selected as predetermined points on the waveform with respect to various morphological characteristics such as sign changes or zero crossings in the waveform, or samples at particular times following the stimulation pulse.

Time interval evoked response parameters include intervals from stimulation to peak positive and/or negative amplitude response values or to zero-crossings, intervals from negative to positive peak values, intervals from zero-crossing to peak levels, and the like. Other suitable intervals are commenced or terminated on peak derivative values.

The evoked response parameter processing operation 422 may also include signal processing functionality such as fast fourier transform (FFT) or other transform capabilities for converting time domain signals into frequency domain signals for subsequent analysis. Analysis of frequency domain coefficients correlates to autonomic nervous system tone on the basis that changes in evoked response morphology result in changes in frequency content that are diagnostic of myocardial condition.

Once the evoked response signal is converted to a frequency representation, frequency domain features can be determined for one or more frequencies or frequency bands. If selected, one or more frequency domain evoked response parameters may be computed from the transformed data. For example, power may be computed, typically by squaring frequency domain samples and possibly scaling the squared values. The overall power content for the signal may be determined or power levels in selected frequency bands. The evoked response parameter processing operation 422 may access power levels in multiple frequency bins and divide one power sample by another to determine ratios of power levels in different frequency bands.

The evoked response parameter processing operation 422 can determine frequency domain parameters using various techniques. In one example, a signal from a single evoked response complex can be acquired, transformed, and converted to a power signal. In another example, multiple evoked response complexes can be acquired over a plurality of cardiac cycles, either sequential or sampled, summed and ensemble-averaged, then converted to the frequency domain.

In another example, the evoked response parameter processing operation 422 estimates power spectral density of the evoked response signal using periodograms of stored intracardiac electrograms (IEGM) containing only evoked response measurements. During signal acquisition, the processor 260 designates the cardiac cycles as either stimulated or intrinsic cycles. The processor 260 may be configured to store a specified number of samples of stimulated cycle data, intrinsic cycle data, both types of data, or neither type. For a stimulated cycle, the signal is typically stored beginning at a preselected time interval following delivery of a pacing pulse. Samples from a plurality of cardiac cycles are placed in a time window, summed within that window, and stored for computation of a periodogram. The periodogram uses a multiple-point fast fourier transform (FFT) of windowed data for computation. Data can be either wrapped or zero-filled depending on the size of the FFT and the size of the data window.

In a measurement postfiltering action 426, the processor 260 may filter measurements that are out-of-range in comparison to the most recent history of measurements.

In a trend or tendency analysis action 430, the processor 260 performs control operations that determine trends or tendencies in evoked response characteristics that vary over time. In early stages of the evoked response analysis, baseline data are acquired, processed, and stored that are indicative of an initial myocardial or autonomic tone or condition. The baseline data may be a single sample or a combination of multiple samples. The baseline data may be acquired and stored automatically, manually under control of a clinician, or any combination of automatic and manual operations. A single baseline data sample may be stored or multiple samples taken over time may be stored to more definitely show changes and trends in evoked response parameters. For samples taken subsequent to the early stages of analysis, the trend or tendency analysis action 430 compares the current sample to the baseline data and any other stored history of samples and may determine a therapeutic action in response to the analysis of current and history data.

The stimulation device 110 may be configured to acquire a daily measurement that may be performed at approximately the same time each day, or to acquire samples more or less often than once per day. For example, the stimulation device 110 may be configured to acquire samples once per hour or more often.

Samples may be acquired in any of several forms. For example, the daily measurement may be an evoked response amplitude measurement and the mean and standard deviation of the amplitude may be stored. A decreasing mean amplitude is indicative of progression of heart failure. An increasing standard deviation may also be indicative of the progression of heart failure. In other examples, evoked response slope or various timing parameters may be tracked.

In another example, a 24-hour histogram of evoked response amplitude measurements may be acquired. Daily changes in autonomic tone are monitored by analysis of histogram characteristics such as width and tendency of the histogram of measurements acquired at the same time of the day.

An update history action 132 optionally or selectively stores the current sample as part of the evoked response data history. The current sample may be stored as part of the data history along with any other pertinent data including current cardiac rate AV-delay, QT or Stim-T interval, and the like.

A deliver therapy action 434 may selectively be activated for some or all measurements, or may be activated asynchronous to the monitoring operation. The therapy is typically a stimulation therapy but may include other types of therapy such as a drug therapy that is administered by generation of signals to an infusion pump that supplies a therapeutic medication. Stimulation therapy includes adjustment of stimulation cycle to change stimulation frequency, adjustment of chamber delay intervals such as AV/PV intervals, V—V timing, and management of stimulation delivery in different parts of the heart. In a stimulation device 110 configured for biventricular pacing, the deliver therapy action 434 may activate biventricular pacing or adjust timing of biventricular pacing to improve myocardial condition.

The stimulation device 110 can perform cardiac physiology monitoring for controlling therapy, operating as a control system for modifying stimulation rate to improve autonomic tone and enhance the evoked response.

The stimulation device 110 can optimize hemodynamics for treatment of heart failure by monitoring heart failure progression for a stimulating device configured for biventricular pacing. Biventricular pacing has been demonstrated to improve heart condition including enhancements in both symptoms and quality of life in some patients with heart failure. Possibly, the improvement in myocardial tone from biventricular pacing results because such pacing produces a more coordinated pattern of contraction than dissynchronous ventricular activity that occurs in patients with interventricular conduction defects. Evoked response monitoring can be used to determine stimulation timing and rates that improve myocardial tone.

The delivery therapy action 434 may adjust any of the evoked response operations including adjustment of acquisition time and acquisition frequency using a control action that accounts for the data history, the current measurement, and any other conditions. For example, the time of day at which the measurement is made may be controlled to optimize the evoked response measurement. The cardiac rate and AV-delay may also be adjusted to improve myocardial tone, while held within a standardized range to acquire reproducible measurement data.

In one example, the daily measurement time can be adjusted based on evoked response amplitude or integral measurements, and QT or stimulation-T wave interval measurements. The acquisition time is varied in small increments over time and data is stored for the samples including: (1) time of day, (2) evoked response measurement result, and (3) QT interval duration. A control operation adjusts the acquisition time to produce the largest evoked response amplitude or integral that has the longest QT interval.

Figure 5:
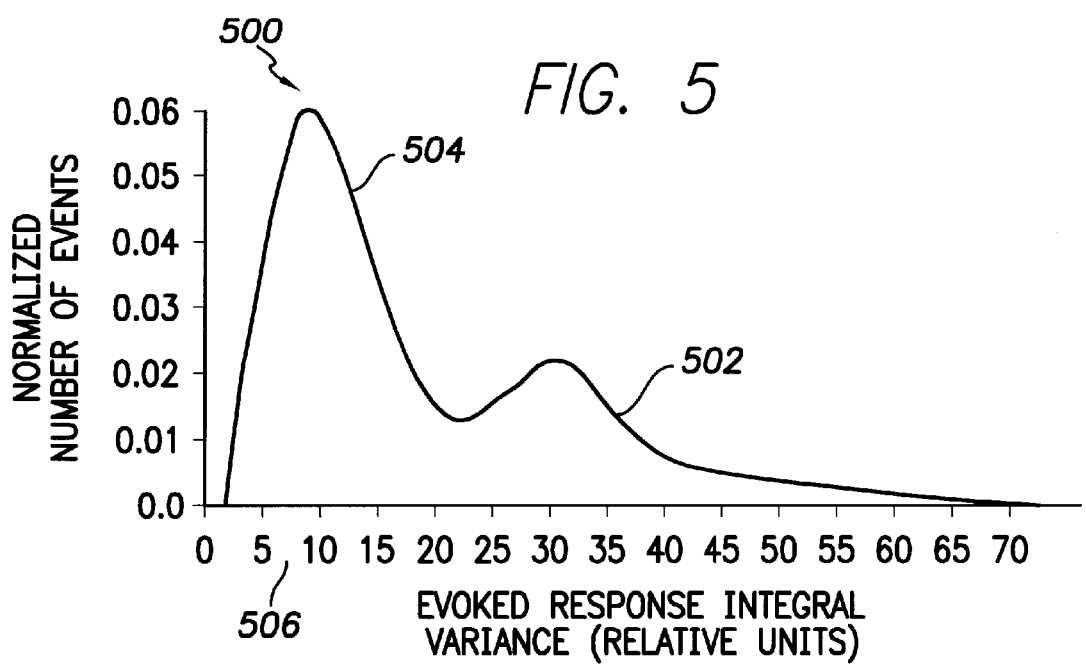
FIG. 5 is a graphic representation of an evoked response parameter variability histogram used as an indicator of autonomic tone and surrogate for patient condition.

FIG. 5 shows an example of an evoked response parameter variability histogram 500 containing data collected over a period of about one week for a typical patient. Form of the histogram varies depending on the particular evoked response parameter that is measured such as amplitude, slope, integral, time intervals, or frequency domain power and power ratios. Histogram data can be accumulated in the trend or tendency analysis action 430 described in the discussion of FIG. 4. The evoked response variability histogram is maintained in the memory 294.

In one example, evoked response is periodically and repeatedly sensed and integrated. A statistical analysis action determines parameters such as mean, mode, and variability measures of variance or standard deviation. Data relating to one or more of the statistical parameters can be arranged into histograms for additional analysis. In a specific example, a variance parameter can be arranged into an evoked response integral variance histogram 500 that is divided into 128 two-byte bins, each corresponding to an evoked response integral variance value so that the evoked response integral variance histogram 500 occupies 256 bytes of memory 294.

The evoked response integral variance histogram 500 typically is characterized by a bimodal distribution with higher mode 502 corresponding to evoked response integral variance measurements acquired when the patient's autonomic tone is elevated, typically when the patient is most alert. A lower mode 504 is a dominant mode and corresponds to evoked response integral variance measurements acquired when the patient is relatively inactive including resting times and during sleep.

A bin 506 of evoked response integral variance histogram 500 is designated by the variable evoked response integral threshold. The bin 506 is estimated to be the highest bin of evoked response integral variance histogram 500 that contains evoked response integral variance measurements acquired for the relatively inactive patient.

Figure 6:
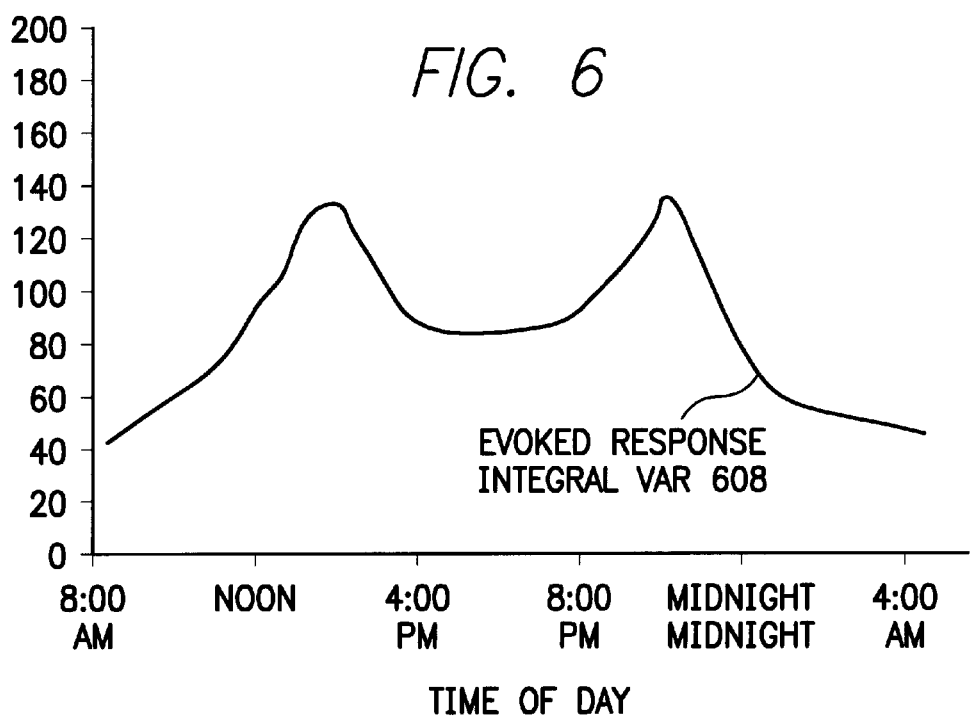
FIG. 6 is a graph showing a plot of evoked response parameter variability values used to derive the indicator of autonomic tone for diagnosis and application of therapy.

Referring to FIG. 6, a graph depicts an example of a plot of evoked response integral values showing circadian variations during the day. The graph shows a plot of evoked response integral variance measurements 608 derived by processor 260 over a 24 hour period. In the example, during waking hours from approximately 8:00 AM to about 11:00 PM, the patient is awake and occasionally active, and evoked response integral variance measurements are relatively high with particular high levels immediately upon waking and late in the day.

At about 11:00 PM, the patient begins sleep and the plotted evoked response integral variance measurements 608 show a substantial decline in activity variance to a level. For most of the period from about 11:00 PM to about 5:00 AM, evoked response integral variance maintains at the sleeping rate with some variation at about 3:00 AM resulting from brief activity.

Figure 7:
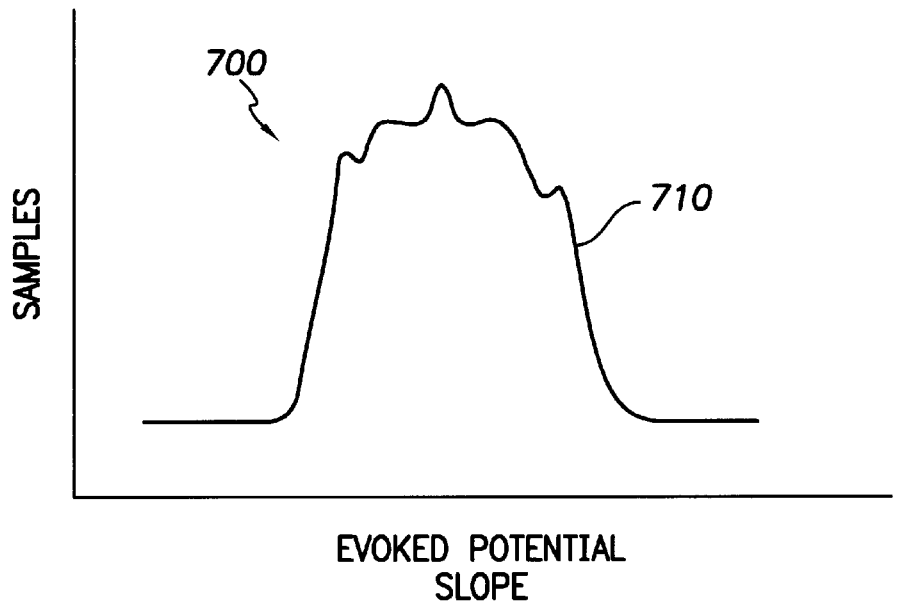
FIG. 7 is a graph that illustrates another example of a technique for tracking patient condition on the basis of evoked response variability.

Referring to FIG. 7, a graph 700 illustrates another example of a technique for tracking patient condition on the basis of evoked response variability. The graph 700 shows a histogram 710 of evoked response slope measurements acquired at predetermined intervals during the day. In some configurations, evoked response slope measurements are acquired periodically throughout a day and a histogram of slopes is accumulated for the entire day. In other configurations, evoked response slope measurements are acquired at particular times during the day and one or more histograms are accumulated that correspond to predefined timing ranges. The histograms are stored as a record of variability of the evoked response slope parameter. A history of histograms is stored so that variability of the evoked response slope parameter can be tracked over time. Changes in the variability parameter over time are indicative of patient condition and autonomic tone.

Figure 8:
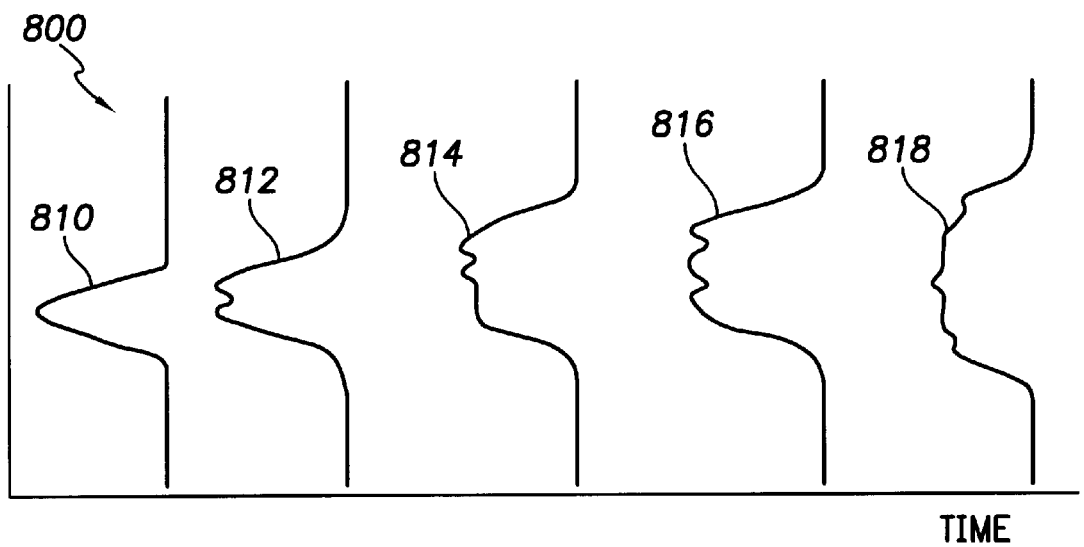
FIG. 8 is a graph that illustrates histograms stored over time to permit tracking of trends.

FIG. 8 is a graph that illustrates histograms 810, 812, 814, 816, and 818 stored over time to permit tracking of trends. In one example, the histograms can be stored each month for several months with a histogram for a new month replacing the oldest stored histogram in a circular buffer fashion.

While the invention has been described with reference to various embodiments, it will be understood that these embodiments are illustrative and that the scope of the invention is not limited to them. Many variations, modifications, additions and improvements of the embodiments described are possible. For example, those of ordinary skill in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. An implantable cardiac stimulation device comprising:
   at least one pulse generator that is capable of generating stimulating pulses to stimulate cardiac tissue;
   at least one sensor that is capable of electrical coupling to the cardiac tissue and sensing an evoked response resulting from an applied stimulating pulse;
   a data storage array; and
   a controller coupled to the at least one pulse generator, the at least one sensor, and the data storage array, the controller comprising an executable control logic that derives at least one parameter from the sensed evoked response, determines variation of the at least one parameter over time, and derives an indicator of patient condition based on the parameter variation.

2. An implantable cardiac stimulation device according to claim 1, wherein the controller monitors an amplitude of the evoked response over time as a surrogate of heart condition to detect progression or regression in heart failure patients.

3. An implantable cardiac stimulation device according to claim 1 further comprising:
   an executable control logic operable in the controller that tracks long-term changes in myocardial condition while filtering circadian and other extraneous influences on measurements comprising cardiac rate, exercise or activity level, and time of day.

4. An implantable cardiac stimulation device according to claim 1 further comprising:
   an executable control logic operable in the controller that derives an indicator of autonomic tone.

5. An implantable cardiac stimulation device according to claim 1 further comprising:
an executable control logic operable in the controller that derives an indicator of myocardial condition.

6. An implantable cardiac stimulation device according to claim 1 further comprising:
an executable control logic operable in the controller that adjusts a cardiac therapy based on the indicator of patient condition.

7. An implantable cardiac stimulation device according to claim 1 further comprising:
an executable control logic operable in the controller that derives at least one parameter of parameters selected from among a group comprising evoked response amplitude, evoked response slope, evoked response integral, and evoked response time intervals.

8. An implantable cardiac stimulation device according to claim 1 further comprising:
an executable control logic operable in the controller that derives frequency domain characteristics from the evoked response and derives at least one parameter of parameters selected from among a group comprising power spectral characteristics in a plurality of frequency bands, ratios between the power spectral characteristics in pairs of the plurality of frequency bands, evoked response amplitude, evoked response slope, evoked response integral, and evoked response time intervals.

9. An implantable cardiac stimulation device according to claim 1 further comprising:
an executable control logic operable in the controller that derives at least one frequency domain characteristic parameter from the evoked response selected from among a group of frequency domain characteristic parameters comprising:
frequency domain parameters calculated from a single evoked response complex, frequency domain parameters calculated from an ensemble of averaged evoked response complexes, and frequency domain parameters calculated from a periodogram of stored intracardiac electrograms containing only evoked responses.

10. An implantable cardiac stimulation device according to claim 1 further comprising:
a timer coupled to the controller; and
an executable control logic operable in the controller that determines a time-to-zero-crossing parameter of a bipolar evoked response and a slope parameter of the bipolar evoked response, derives a parameter indicative of conduction velocity from the time-to-zero-crossing parameter and the slope parameter, and stores a time history of the time-to-zero-crossing parameter and the slope parameter as a metric for autonomic nervous system effects on myocardial state.

11. An implantable cardiac stimulation device according to claim 1 further comprising:
a timer coupled to the controller; and
an executable control logic operable in the controller that concurrently determines cardiac rate and AV/PV delay values for evoked cardiac cycles and stores the cardiac rate and AV/PV delay values in time correspondence with the time history of one or more of the parameters.

12. An implantable cardiac stimulation device according to claim 1 further comprising:
an executable control logic operable in the controller that derives at least one variability statistic indicative of time variability of the parameter time history of one or more of the parameters and diagnostic of patient condition and adjusts a cardiac therapy based on one or more of the variability statistics.

13. An implantable cardiac stimulation device according to claim 1 further comprising:
an executable control logic operable in the controller that derives at least one variability statistic indicative of time variability of the parameter time history of one or more of the parameters and diagnostic of patient condition and automatically adjusts aggressiveness of overdrive pacing based on one or more of the variability statistics.

14. An implantable cardiac stimulation device according to claim 1 further comprising:
an executable control logic operable in the controller that derives at least one variability statistic indicative of time variability of the parameter time history of one or more of the parameters and diagnostic of patient condition and automatically adjusts pacing to lower circadian rates to promote intrinsic cardiac activity based on one or more of the variability statistics.

15. An implantable cardiac stimulation device according to claim 1 further comprising:
an executable control logic operable in the controller that derives at least one variability statistic indicative of time variability of the parameter time history of one or more of the parameters and diagnostic of patient condition and automatically adjusts AV and PV delays to promote intrinsic cardiac activity based on one or more of the variability statistics.

16. An implantable cardiac stimulation device according to claim 1 wherein the evoked response is an atrial evoked response.

17. An implantable cardiac stimulation device according to claim 1 wherein the evoked response is a ventricular evoked response.

18. An implantable cardiac stimulation device according to claim 1 further comprising:
a telemetry transmitter and receiver coupled to the controller and capable of communicating an indicator of parameter variation to an external programmer.

19. An implantable cardiac stimulation device according to claim 1 further comprising:
an executable control logic operable in the controller that controls an automatic capture functionality.

20. An implantable cardiac stimulation device according to claim 1 further comprising:
an executable control logic operable in the controller that measures and tracks myocardial condition over time using a diurnal sensor that triggers a measurement at a consistent, suitable time at regular intervals such as one or more times per day or week.

21. An implantable cardiac stimulation device according to claim 1 further comprising:
an executable control logic operable in the controller that acquires a 24-hour histogram of evoked response measurements and monitors daily change in autonomic tone is monitored by analysis of histogram characteristics such as width and tendency of the histogram at the same time of the day.

22. An implantable cardiac stimulation device according to claim 1 further comprising:
an executable control logic operable in the controller that performs cardiac physiology monitoring for controlling therapy, and operates as a control system for modifying stimulation rate to improve autonomic tone and enhance the evoked response.

23. An implantable cardiac stimulation device comprising:
   at least one pulse generator that is capable of generating stimulation energy to be delivered to cardiac tissue;
   at least one sensor that is capable of sensing an evoked response resulting from applied stimulation energy; and
   a controller coupled to the at least one pulse generator and to the at least one sensor, the controller being operative to derive at least one parameter from the sensed evoked response, determine variation of the at least one parameter over time, and derive an indicator of patient condition based on the parameter variation.

24. A method of operating an implantable cardiac stimulation device comprising:
   delivering stimulation energy to cardiac tissue;
   sensing an evoked response of the cardiac tissue;
   deriving at least one parameter from the evoked response;
   determining variation of the at least one parameter over time; and
   deriving an indicator of patient condition based on the parameter variation.

25. A method according to claim 24 further comprising:
   adjusting a patient therapy based on the parameter variation.

26. A method according to claim 24 further comprising:
   adjusting a cardiac therapy based on the parameter variation.

27. A method according to claim 24 further comprising:
   communicating a derived parameter to an external programmer.

28. A method according to claim 24 further comprising:
   deriving at least one variability statistic indicative of variation of the at least one parameter over time;
   automatically diagnosing a patient condition from the at least one variability statistic; and
   adjusting a cardiac therapy based on the patient condition and the at least one variability statistic.

29. A method according to claim 24 wherein:
   deriving at least one parameter from the evoked response further comprises:
      measuring an evoked response amplitude.

30. A method according to claim 24 wherein:
   deriving at least one parameter from the evoked response further comprises:
      measuring an evoked response slope.

31. A method according to claim 24 wherein deriving at least one parameter from the evoked response further comprises:
   integrating the evoked response.

32. A method according to claim 24 wherein deriving at least one parameter from the evoked response further comprises:
   timing at least one time interval in an evoked response signal sequence.

33. A method according to claim 24 wherein deriving at least one parameter from the evoked response further comprises:
   acquiring a single evoked response complex; and
   converting the single evoked response complex to a frequency domain signal.

34. A method according to claim 24 wherein deriving at least one parameter from the evoked response further comprises:
   acquiring a plurality of evoked response complexes;
   time aligning the plurality of evoked response complexes;
   averaging the plurality of time aligned evoked response complexes to form an averaged evoked response signal; and
   converting the averaged evoked response signal to a frequency domain signal.

35. A method according to claim 24 wherein deriving at least one parameter from the evoked response further comprises:
   acquiring a plurality of intracardiac electrograms containing only evoked responses;
   assembling the intracardiac electrograms into a periodogram; and
   converting the periodogram to a frequency domain signal.

36. A method according to claim 24 wherein deriving at least one parameter from the evoked response further comprises:
   acquiring a bipolar evoked response;
   timing events of the bipolar evoked response;
   determining a time-to-zero-crossing parameter of the bipolar evoked response;
   determining a slope parameter of the bipolar evoked response;
   deriving a parameter indicative of conduction velocity from the time-to-zero-crossing parameter and the slope parameter;
   storing a time history of the time-to-zero-crossing parameter and the slope parameter as a metric for autonomic nervous system effects on myocardial state; and
   deriving a variability statistic indicative of variation of the time-to-zero-crossing parameter and the slope parameter over time.

37. A method according to claim 24 wherein determining variation of the at least one parameter over time further comprises:
   determining a cardiac rate and AV/PV interval values for evoked cardiac cycles;
   storing the cardiac rate and AV/PV interval values in time correspondence with the parameters; and
   correcting evoked response parameter variation for differences in cardiac rate and AV/PV interval.

38. A method according to claim 24 further comprising:
   deriving at least one variability statistic indicative of time variability of the one or more parameters and diagnostic of patient condition; and
   adjusting a cardiac therapy based on one or more of the variability statistics.

39. A method according to claim 24 further comprising:
   deriving at least one variability statistic indicative of time variability of the one or more parameters and diagnostic of patient condition; and
   adjusting aggressiveness of overdrive pacing based on one or more of the variability statistics without external intervention.

40. A method according to claim 24 further comprising:
   deriving at least one variability statistic indicative of time variability of the one or more parameters and diagnostic of patient condition; and
   adjusting pacing to lower circadian rates to promote intrinsic cardiac activity based on one or more of the variability statistics without external intervention.

41. A method according to claim 24 further comprising:
deriving at least one variability statistic indicative of time variability of the one or more parameters and diagnostic of patient condition; and
adjusting AV and PV delays to promote intrinsic cardiac activity based on one or more of the variability statistics without external intervention.

42. A method according to claim 24 further comprising:
determining a pharmacologic therapy based on the parameter variation.

43. A method according to claim 24 further comprising:
determining an electrical stimulation therapy based on the parameter variation.

44. A method according to claim 24 further comprising:
deriving at least one variability statistic indicative of time variability of the one or more parameters and diagnostic of patient condition; and
determining a pharmacologic therapy based on one or more of the variability statistics.

45. A method according to claim 24 further comprising:
deriving at least one variability statistic indicative of time variability of the one or more parameters and diagnostic of patient condition; and
determining an electrical stimulation therapy based on one or more of the variability statistics.

46. An implantable cardiac stimulation device comprising:
a pulse generator capable of coupling to cardiac tissue for stimulating an evoked response in the cardiac tissue;
a sensor capable of coupling to the cardiac tissue for sensing the evoked response;
a processor coupled to the pulse generator and coupled to the sensor;
a memory coupled to the processor and capable of storing data; and
executable means capable of execution in the processor for executing a sequence of actions further comprising:
means for deriving at least one parameter from the sensed evoked response;
means for determining variation of the at least one evoked response parameter over time; and
means for deriving an indicator of patient condition based on the parameter variation.

47. An implantable cardiac stimulation device according to claim 46 wherein the executable means further comprises:
adjusting means for adjusting a cardiac therapy based on the indicator of patient condition.

48. An implantable cardiac stimulation device according to claim 46 wherein the evoked response parameter deriving means further comprises:
means for measuring an evoked response amplitude from the sensed evoked response.

49. An implantable cardiac stimulation device according to claim 46 wherein the evoked response parameter deriving means further comprises:
means for determining an evoked response slope.

50. An implantable cardiac stimulation device according to claim 46 wherein the evoked response parameter deriving means further comprises:
means for integrating the sensed evoked response to produce an evoked response integral.

51. An implantable cardiac stimulation device according to claim 46 wherein the evoked response parameter deriving means further comprises:
means for determining one or more evoked response time intervals.

52. An implantable cardiac stimulation device according to claim 46 wherein the evoked response parameter deriving means further comprises:
means for transforming the sensed evoked response to a frequency domain signal; and
means for determining power spectral characteristics of the frequency domain signal in a plurality of frequency bands.

53. An implantable cardiac stimulation device according to claim 46 wherein the evoked response parameter deriving means further comprises:
means for transforming the sensed evoked response to a frequency domain signal;
means for determining power spectral characteristics of the frequency domain signal in a plurality of frequency bands; and
means for determining ratios between the power spectral characteristics in pairs of the plurality of frequency bands.

54. An implantable cardiac stimulation device according to claim 46 wherein the evoked response parameter deriving means further comprises:
means for transforming a single evoked response complex to a frequency domain signal.

55. An implantable cardiac stimulation device according to claim 46 wherein the evoked response parameter deriving means further comprises:
means for aligning the plurality of evoked response complexes in time;
means for averaging a plurality of evoked response complexes; and
means for transforming the averaged evoked response complex to a frequency domain signal.

56. An implantable cardiac stimulation device according to claim 46 wherein the evoked response parameter deriving means further comprises:
means for acquiring a plurality of intracardiac electrograms containing only evoked responses;
means for assembling the intracardiac electrograms into a periodogram; and
means for transforming the periodogram to a frequency domain signal.

57. An implantable cardiac stimulation device according to claim 46 further comprising:
a clock coupled to the processor for timing cardiac cycle events, wherein the evoked response parameter deriving means further comprises:
means for timing a time-to-zero-crossing parameter of a bipolar evoked response;
means for determining a slope parameter of the bipolar evoked response;
means for deriving a parameter indicative of conduction velocity from the time-to-zero-crossing parameter and the slope parameter; and
means for tracking time variations in the time-to-zero-crossing parameter and the slope parameter as a metric for autonomic nervous system effects on myocardial state.

58. An implantable cardiac stimulation device according to claim 46 further comprising:
a clock coupled to the processor for timing cardiac cycle events, wherein the evoked response parameter deriving means further comprises:

means for concurrently determining cardiac rate and AV/PV delay values for evoked cardiac cycles; and means for time correlating the cardiac rate and AV/PV delay values with the one or more evoked response parameters.

59. An implantable cardiac stimulation device according to claim 46 wherein the executable means further comprises:

variability deriving means for deriving at least one variability statistic indicative of variation of the at least one evoked response parameter over time; and means for adjusting a cardiac therapy based on one or more of the variability statistics.

60. An implantable cardiac stimulation device according to claim 46 wherein the executable means further comprises:

variability deriving means for deriving at least one variability statistic indicative of variation of the at least one evoked response parameter over time; and means for adjusting aggressiveness of overdrive pacing based on one or more of the variability statistics without external intervention.

61. An implantable cardiac stimulation device according to claim 46 wherein the executable means further comprises:

variability deriving means for deriving at least one variability statistic indicative of variation of the at least one evoked response parameter over time; and means for adjusting pacing to lower circadian rates to promote intrinsic cardiac activity based on one or more of the variability statistics without external intervention.

62. An implantable cardiac stimulation device according to claim 46 wherein the executable means further comprises:

variability deriving means for deriving at least one variability statistic indicative of variation of the at least one evoked response parameter over time; and means for adjusting AV and PV delays to promote intrinsic cardiac activity based on one or more of the variability statistics without external intervention.

63. An implantable cardiac stimulation device according to claim 46 further comprising:

an atrial pulse generator for stimulating an evoked response in atrial cardiac tissue;

atrial sensor capable of coupling to the atrial cardiac tissue for sensing the atrial evoked response.

64. An implantable cardiac stimulation device according to claim 46 further comprising:

ventricular pulse generator for stimulating an evoked response in ventricular cardiac tissue;

ventricular sensor capable of coupling to the ventricular cardiac tissue for sensing the ventricular evoked response.

65. An implantable cardiac stimulation device according to claim 46 further comprising:

telemetry means coupled to the execution means for communicating one or more of the parameters to an external programmer.

66. An implantable cardiac stimulation comprising:

means for providing stimulation energy to cardiac tissue;

means for deriving at least one parameter from an evoked response signal;

means for determining a variation of the at least one parameter over time; and means for deriving an indicator of patient condition based on the parameter variation.

* * * * *